United States Patent [19]

Zentner et al.

[11] Patent Number: 4,968,507
[45] Date of Patent: * Nov. 6, 1990

[54] CONTROLLED POROSITY OSMOTIC PUMP

[75] Inventors: Gaylen M. Zentner; Gerald S. Rork, both of Lawrence, Kans.; Kenneth J. Himmelstein, Irvine, Calif.

[73] Assignee: Merck & Co., Inc., Rahway, N.J.

[*] Notice: The portion of the term of this patent subsequent to Jul. 25, 2006 has been disclaimed.

[21] Appl. No.: 73,781

[22] Filed: Jul. 15, 1987

Related U.S. Application Data

[63] Continuation-in-part of Ser. No. 850,576, Apr. 11, 1986, abandoned, which is a continuation of Ser. No. 689,540, Jan. 7, 1985, abandoned, which is a continuation-in-part of Ser. No. 622,808, Jun. 20, 1984, abandoned.

[51] Int. Cl.$^5$ .............................................. A61K 9/64
[52] U.S. Cl. .................................. 424/465; 604/890.1; 604/892.1; 424/473
[58] Field of Search ........................ 424/465, 473; 604/890.1, 892.1

[56] References Cited

U.S. PATENT DOCUMENTS 3,538,214 11/1970 Polli et al. ............................ 424/473
3,845,770 11/1974 Theeuwes et al. .................. 424/469
3,916,899 11/1975 Theeuwes et al. .................. 424/469
4,160,452 7/1979 Theeuwes ............................ 424/469
4,200,098 4/1980 Ayer et al. ........................... 424/424
4,256,108 3/1981 Theeuwes ............................ 424/469
4,285,987 8/1981 Ayer et al. ............................. 427/3
4,557,925 12/1985 Lindahl et al. ...................... 424/469
4,687,660 8/1987 Baker et al. .......................... 424/465
4,851,228 7/1989 Zentner et al. ...................... 424/456

Primary Examiner—Ronald W. Griffin
Attorney, Agent, or Firm—Kevin J. McGough; Joseph F. DiPrima; Michael C. Sudol, Jr.

[57] ABSTRACT

The instant invention is directed to an osmotic pump comprising:

(A) at least one active agent surrounded by (B) a rate controlling water insoluble wall, having a fluid permeability of $6.96 \times 10^{-18}$ to $6.96 \times 10^{-14}$ cm$^3$ sec/g and a reflection coefficient of less than 1, prepared from:

(i) a polymer permeable to water but impermeable to solute and (ii) 0.1 to 60% by weight, based on the total weight of (i) and (ii), of at least one pH insensitive pore forming additive dispersed throughout said wall.

17 Claims, 19 Drawing Sheets

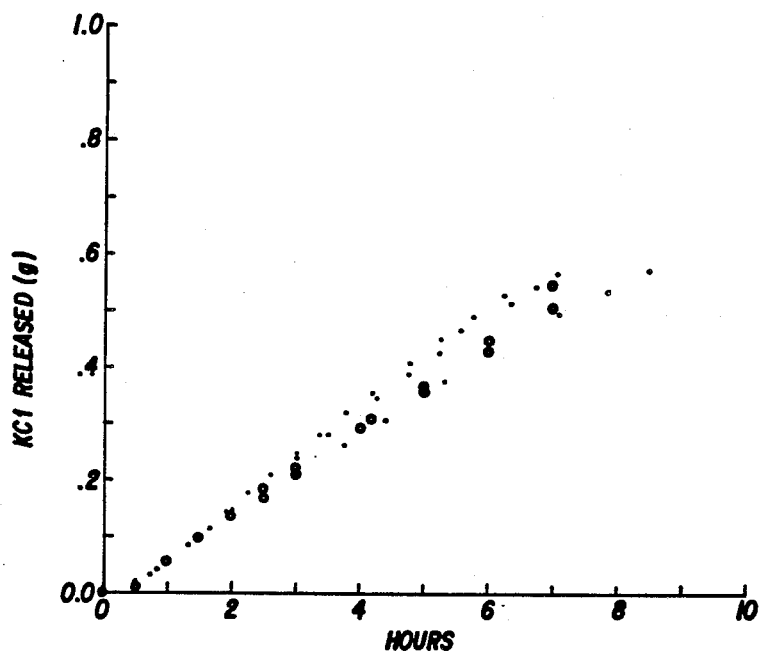
FIG. 3A MMP-10

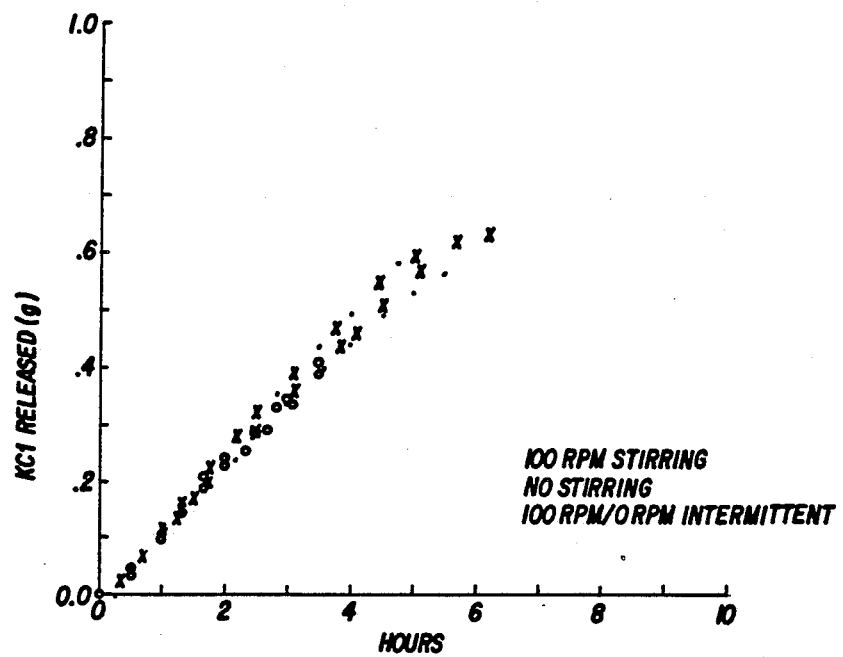
FIG. 3B MMP-25

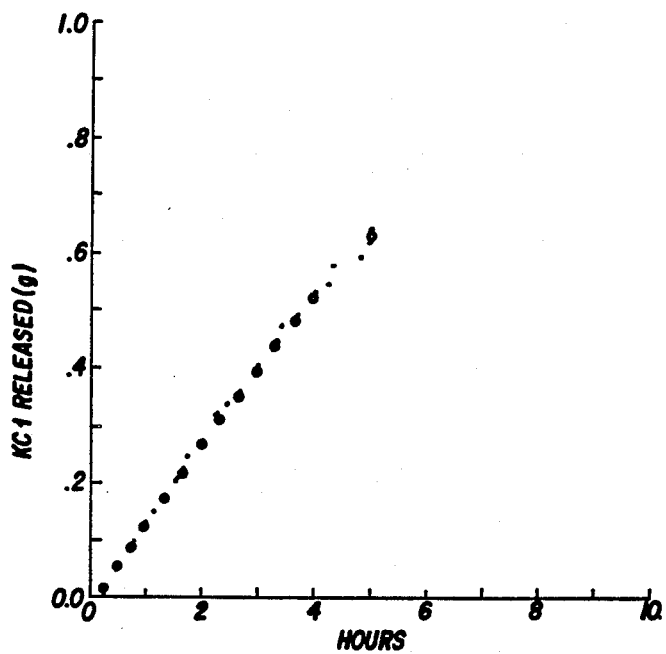
FIG. 3C MMP-50

CONTROLLED POROSITY OSMOTIC PUMP

BACKGROUND OF THE INVENTION

This invention concerns an osmotically activated system for dispensing pharmacologically active agent(s). The system comprises an inner core compartment of osmotically active composition surrounded by an enclosing wall material. The core comprises pharmacologically active agent(s) soluble in an external fluid, or a mixture of agent(s) having a limited solubility in the external fluid with osmotically effective solute(s) that is/are soluble in the fluid, which exhibit an osmotic pressure gradient across the wall against the external fluid. The wall constitutes a layer of controlled porosity that is substantially permeable to both the external fluid and the core composition. Agent is released from the system by fluid imbibition through the wall into the inner core compartment at a rate controlled by the wall composition and dimensions, producing a solution containing agent that is released through the wall at a controlled rate in response to fluid volume flux, $dV/dt$, resulting from the osmotic pressure gradient, and diffusive flux, $(dM/dt)_D$, driven by the chemical potential gradient of the agent across the wall. The total rate of agent release, $(dM/dt)_T$, is given by Equation 1 where C is the concentration $$\left(\frac{dM}{dt}\right)_T = \left(\frac{dV}{dt}\right)_{(C)} + \left(\frac{dM}{dt}\right)_D \qquad \text{Eq. 1}$$

of the active agent in the dissolved core composition and remains constant when excess solid core mass is present. For the special case where the core mass is pure active agent, the dissolved concentration is equal to the active agent solubility, S, in the fluid. In the present invention the volume flux contribution, $(dV/dt)C$, to the total rate is greater than the diffusive contribution, $(dM/dt)_D$, and forms the basis for the osmotic pump action of the device.

The object of this invention is to provide an osmotically actuated system for controlled delivery of pharmacologically active agents to biological receptor sites over a prolonged period of time.

The controlled porosity wall of the present invention is substantially permeable to both solute and external fluid. The wall is composed of materials that maintain their physical and chemical integrity during the controlled dispensing of agent in mixture with materials that can be leached into the external fluid. The wall has programmable fluid transmission and agent release rates which provide for controlled release of agent which is free from environmental influences including pH and degree of external fluid agitation.

The wall may be composed of either insoluble, non-erodible materials mixed with leachable additives, or bioerodible materials containing leachable additives. Bioerodible materials would be selected to bioerode after a predetermined period with bioerosion occurring subsequent to the period of agent release.

Another object of the invention is to provide an osmotic system that is readily manufactureable to deliver a pre-determined dose of agent at a programmed rate from compositions of matter in the varied geometries and sizes of tablets, pellets, multi-particulates, and such related dosage forms as familiar to those skilled in the art for oral, buccal, vaginal, rectal, nasal, ocular, aural, parenteral and related routes of administration. Another object of the invention is to provide an osmotic system that delivers agent on an equivalent mass per unit surface area basis.

The use of pore formers in substantially water impermeable polymers, such as polyvinyl chloride, is disclosed in J. Pharm. Sci. 72, 772-775 and U.S. Pat. No. 4,244,941. These devices are not osmotic pumps. The devices release the core contents by simple diffusion through the pores in the coating.

U.S. Pat. No. 3,957,523 discloses a device which has pH sensitive pore formers in the wall.

U.S. Pat. Nos. 4,256,108; 4,160,452; 4,200,098 and 4,285,987 disclose devices with pore formers in only one of at least two wall layers. These devices contain a drilled hole for the release of the core contents.

A BRIEF DESCRIPTION OF THE DRAWINGS

FIGS. 3, 4, 6, 7 and 9 through 16 are the release profiles of the pumps produced in Examples 4 through 15, respectively.

Figure 5:
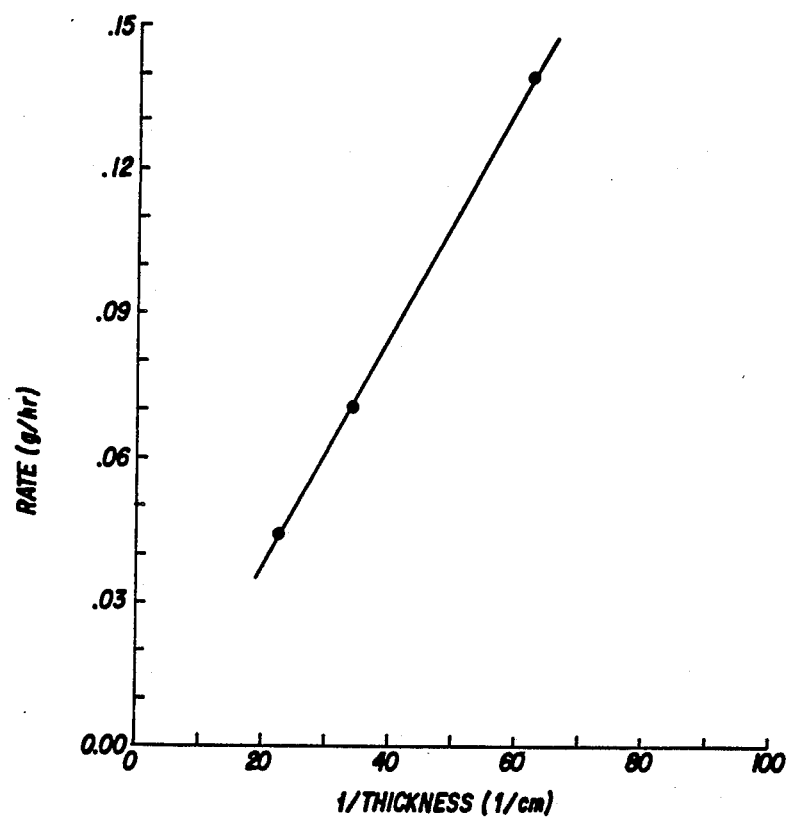

FIG. 5 is a plot of 1/(wall thickness) versus mean release rate of the pumps produced in Example 5.

Figure 8:
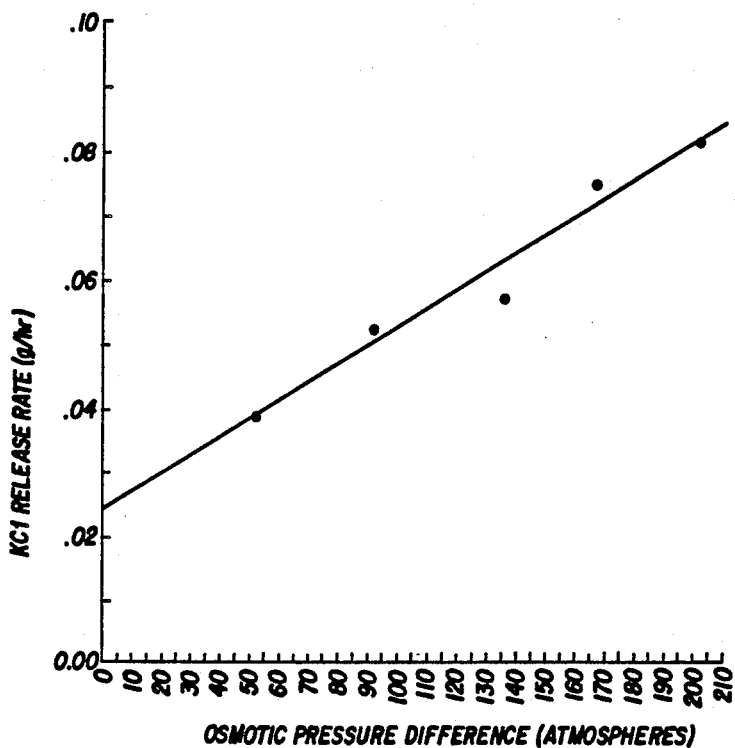

FIG. 8 is a plot of release rate versus the net osmotic pressure difference for the pumps produced in Example 7.

Figure 17:
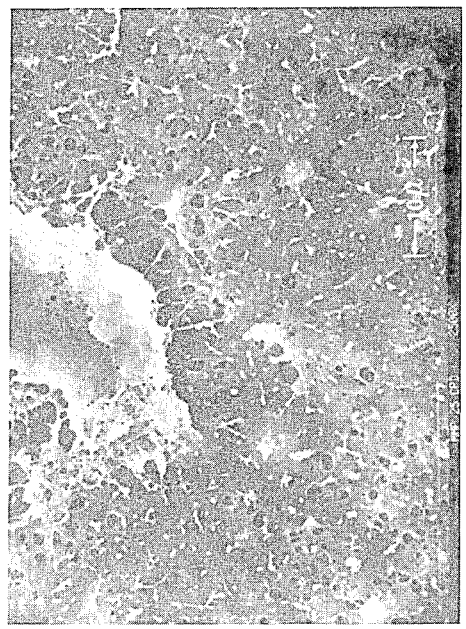

FIG. 17 is a scanning electron micrograph of a leached wall sample from the device described in Example 16, illustrating porosity and pore sizes.

DESCRIPTION OF THE INVENTION

The instant invention is directed to an osmotic pump, comprising:

(A) at least one active agent surrounded by (B) a rate controlling water insoluble wall, having a fluid permeability of $6.96 \times 10^{-18}$ to $6.96 \times 10^{-14}$ cm$^3$ sec/g and a reflection coefficient of less than 1, prepared from:

(i) a polymer permeable to water but impermeable to solute and (ii) 0.1 to 60% by weight, based on the total weight of (i) and (ii), of at least one pH insensitive pore forming additive dispersed throughout said wall.

The phrase "permeable to water but impermeable to solutes" means the water permeates through the polymer preferably to solute, under a pressure differential.

Figure 1:
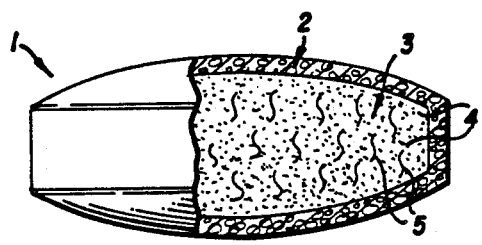
FIG. 1 is an embodiment of the osmotic pump.

Referring to FIG. 1, the osmotic pump device (1) is typically in the form of a single coated tablet or shaped for rectal or vaginal applications, and coated pellets, and multi-particulates having the essential features and elements of FIG. 1, yet of a size such that several such devices may be loaded into a soluble gelatin capsule for oral administrations or suspended in a suitable vehicle for injection or spraying.

The water insoluble, permeable wall (2) of controlled porosity may be applied to osmotically active core composition masses (3) by spray coating procedures. The wall is comprised of (a) polymeric material that is insoluble in the fluids of the environment of intended use (usually water); (b) other added excipients that will dissolve in the environmental fluids and leach out of the wall. Referring to FIG. 17, the leached wall is a sponge-like structure composed of numerous open and closed cells that form a discontinuous interwoven network of void spaces when viewed with a scanning electron microscope. This controlled porosity wall serves as both the water entry and core composition solution exit sites. The wall is permeable to both water and solutes, and as constituted in the environment of use has a small solute reflection coefficient, $\sigma$, and displays poor semipermeable characteristics when placed in a standard osmosis cell.

The specifications for the wall are summarized below and include:

| | |
|---|---|
| 1. Fluid Permeability of the wall | $6.96 \times 10^{-18}$ to $6.96 \times 10^{-14}$ cm$^3$ sec/g (equivalent to $10^{-5}$ to $10^{-1}$ cm$^3$mil/cm$^2$ hr atm) |
| 2. Reflection Coefficient | Microporous coats to have a relfection coefficient, $\sigma$, defined as: $$\sigma = \frac{\text{hydrostatic pressure difference} \times \text{osmotic volume flux}}{\text{osmotic pressure difference} \times \text{hydrostatic volume flux}}$$ where $\sigma$ is less than 1, usually 0 to 0.8. |

A specific embodiment of the present invention are those osmotic pumps wherein the reflection coefficient of the wall is less than 0.5. Exemplifying this embodiment are those osmotic pumps wherein the reflection coefficient of the wall is less than 0.1.

Additional, preferred specifications for the wall include:

| | |
|---|---|
| 1. Plasticizer and Flux Regulating Additives | 0 to 50, preferably 0.001 to 50, parts per 100 parts wall material |
| 2. Surfactant Additives | 0 to 40, preferably .001 to 40, parts per 100 parts wall material |
| 3. Wall Thickness | 1 to 1,000, preferably 20 to 500, microns typically although thinner and thicker fall within the invention |
| 4. Microporous Nature | 5% to 95% pores between 10 angstroms and 100 microns diameter |
| 5. Pore forming Additives | 0.1 to 60%, preferably 0.1 to 50%, by weight, based on the total weight of pore forming additive and polymer, pH insensitive pore forming additive, preferably: (a) 0.1 to 50%, preferably 0.1 to 40%, by weight solid additive (b) 0.1 to 40% by weight liquid additive But no more than 60% total pore formers. |

The water insoluble wall of the instant invention must not be covered on its inner or outer surface by a layer of material that is impermeable to dissolved solutes within the core during the period of pumping operation.

Any polymer permeable to water but impermeable to solutes as previously defined may be used. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethyl cellulose hydroxylated ethylenevinylacetate, poly (ortho ester)s, polyacetals, semipermeable polyglycolic or polylactic acid and derivatives thereof, selectively permeable associated polyelectrolytes, polymers of acrylic and methacrylic acid and esters thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from Polymeric epoxides, copolymers of alkylene oxides and alkyl glycidyl ethers, polyurethanes, and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common*

*Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous Path and the porosity which relates to the size and number of pores. The pore size of a microporous lamina is easily ascertained by measuring the observed pore diameter at the surface of the material under the electron microscope as shown in FIG. 17. Generally, materials possessing from 5% to 95% pores and having a pore size of from 10 angstroms to 100 microns can be used.

Any pH insensitive pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers than can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts such as calcium chloride, calcium nitrate, and the like. The transition metal salts such as ferric chloride, ferrous sulfate, zinc sulfate, cupric chloride, and the like. Water may be used as the pore-former. The pore-formers include organic compounds such as saccharides. The saccharides include the sugars sucrose, glucose, fructose, mannose, galactose, aldohexose, altrose, talose, lactose, monosaccharides, disaccharides, and water soluble polysaccharides. Also, sorbitol, mannitol, organic aliphatic and aromatic ols, including diols and polyols, as exemplified by polyhydric alcohols, poly(alkylene glycols), polyglycols, alkylene glycols, poly($\alpha$-$\omega$)alkylenediols esters or alkylene glycols poly vinylalcohol, poly vinyl pyrrolidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of inorganic and organic salts, carbohydrates, polyalkylene glycols, poly($\alpha$-$\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

It is generally desirable from a preparation standpoint to mix the polymer in a solvent. Exemplary solvents suitable for manufacturing the wall of the osmotic device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone-methanol (80:20), acetone-ethanol (90:10), methylene dichloride-methanol (80:20), nitroethane-ethanol (50:50), nitroethane-ethanol (80:20), ethyl acetate-ethanol (80:20), ethylene dichloride-methanol (80:20), methylenedichloride-methanol (78:22), acetone-water (90:10), chloroform-ethanol (80:20), methylenedichloride-ethanol (79:21), methylene chloridemethanol-water (75:22:3), carbontetrachloridemethanol (70:30), expressed as (weight:weight), and the like.

Exemplary plasticizers suitable for the present purpose include plasticizers that lower the temperature of the second-order phase transition of the wall or the elastic modulus thereof; and also increase the workability of the wall, its flexibility and its permeability to fluid. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, di-(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methyoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toluene) sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their strong tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter X, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability of flux through the wall. The agent can be preselected to increase or decrease the liquid flux. Agents that produce a marked increase in permeability to fluid such as water, are often essentially hydrophilic, while those that produce a marked decrease to fluids such as water, are essentially hydrophobic. The flux regulators in some embodiments also can increase the flexibility and porosity of the lamina. Examples of flux regulators include polyhydric alcohols and derivatives thereof, such as polyalkylene glycols of the formula H-(O-alkylene)$_n$-OH wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula H—(OCH$_2$CH$_2$)$_n$—OH wherein n is respectively 5 to 5.7, 8.2 to 9.1, 12.5 to 13.9, 29 to 36, 29.8 to 37, 68 to 84, and 158 to 204. Other polyglycols include the low molecular weight glycols such as polypropylene, polybutylene and polyamylene.

Additional flux regulators include poly ($\alpha,\omega$)alkylenediols wherein the alkylene is straight or branched chain of from 2 to 10 carbon atoms such as poly(1,3)-propanediol, poly(1,4)butanediol, poly(1,5)pentanediol and poly(1,6)hexanediol. The diols also include aliphatic diols of the formula HOC$_n$H$_{2n}$OH wherein n is from 2 to 10 and diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO-(alkylene-O)$_n$-H wherein the divalent alkylene radical includes the straight chain groups and the isomeric forms thereof having from 2 to 6 carbons and n is 1 to 14. The esters and polyesters are formed by reacting the glycol with either a monobasic or dibasic acid. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present purpose are those surfactants, when added to a wall forming material and other materials, aid in producing an integral composite that is useful for making the operative wall of a device. The surfactants act by regulating the surface energy of materials to improve their blending into the composite. This latter material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric, and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic surfactants such as primary, secondary, tertiary and quaternary alkylammonium salts; acylated polyamines; and salts of heterocyclic amines, arylammonium surfactants such as esters of polyhydric alcohols; alkoxylated amines; polyoxyalkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

Typical surfactants include polyoxyethylenated glycerol ricinoleate; polyoxyethylenated castor oil having from 9 to 52 moles of ethylene oxide; glycerol mannitan laurate, and glycerol (sorbitan oleates, stearates or laurates); polyoxyethylenated sorbitan laurate, palmitate, stearate, oleate or hexaolate having from 5 to 20 moles of ethylene oxide; mono-, di- and poly-ethylene glycol stearates, laurates, oleates, myristates, behenates or ricinoleates; propylene glycol carboxylic acid esters; sorbitan laurate, palmitate, oleate, and stearate; polyoxyethylenated octyl, nonyl, decyl, and dodecylphenols having 1 to 100 moles of ethylene oxide; polyoxyethylenated nonyl, lauryl, decyl, cetyl, oleyl and stearyl alcohols having from 3 to 50 moles of ethylene oxide; polyoxypropylene glycols having from 3 to 300 moles of ethylene oxide; sodium salt of sulfated propyl oleate; sodium di-(heptyl)-sulfosuccinate; potassium xylenesulfonate; 1:1 myristic acid diethanolamide; N-coco-$\beta$-aminopropionic acid; bis-(2-hydroxyethyl)-tallowamine oxide; (diisobutyl-phenoxyethoxyethyl)dimethylbenzylammonium halide; N,N'-polyoxypropylenated ethylenediamine having a molecular weight from 500 to 3000; tetra-alkylammonium salts with up to 26 carbon atoms in the cation; sodium or potassium salt of polypeptide cocoanut, oleic or undecylenic acid condensate; metal salts of N-acylated short chain aminosulfonic acids, soybean phosphatides; and sulfobetaine.

Suitable surfactants can be selected from the above and from other surfactants for blending with wall forming materials by using the surfactant's hydrophile-lipophile balance number, HLB. This number represents the proportion between the weight percentages of hydrophilic and lipophilic groups in a dispersant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known number, blending it with the materials and observing the results. A homogeneous composite is formed with the correct number, while a heterogeneous mixture indicates a different number is needed. This new number can be selected by using the prior number as a guide. The HLB number is known to the art for many surfactants, and they can be experimentally determined according to the procedure in *J. Soc. Cosmetic Chem.*, Vol. 1, pages 311 to 326, 1949, or it can be calculated by using the procedure in *J. Soc. Cosmetic Chem.*, Vol. 5, pages 249 to 256, 1954, and in *Am. Perfumer Essent. Oil Rev.*, Vol 65, pages 26 to 29, 1955. Typical HLB numbers are set forth in Table 1. Generally a number of 10 or less indicates lipophilic behavior and 10 or more indicates hydrophilic behavior. Also, HLB numbers are algebraically additive. Thus, by using a low number with a high number, blends of surfactants can be prepared having numbers intermediate between the two numbers. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

TABLE 1

| SURFACTANT | HLB NUMBER |
| --- | --- |
| Sorbitan trioleate | 1.8 |
| Polyoxyethylene sorbitol beeswax | 2.0 |
| Sorbitan tristearate | 2.1 |
| Polyoxyethylene sorbitol hexastearate | 2.6 |
| Ethylene glycol fatty acid ester | 2.7 |
| Propylene glycol fatty acid ester | 3.4 |
| Propylene glycol monostearate | 3.4 |
| Ethylene glycol fatty acid ester | 3.6 |

TABLE 1-continued

| SURFACTANT | HLB NUMBER |
| --- | --- |
| Glycerol monostearate | 3.8 |
| Sorbitan monooleate | 4.3 |
| Propylene glycol monolaurate | 4.5 |
| Diethylene glycol fatty acid ester | 5.0 |
| Sorbitan monopalmitate | 6.7 |
| Polyoxyethylene dioleate | 7.5 |
| Polyoxypropylene mannitol dioleate | 8.0 |
| Sorbitan monolaurate | 8.6 |
| Polyoxyethylene lauryl ether | 9.5 |
| Polyoxyethylene sorbitan monolaurate | 10.0 |
| Polyoxyethylene lanolin derivative | 11.0 |
| Polyoxyethylene glycol 400 monooleate | 11.4 |
| Triethanolamine oleate | 12.0 |
| Polyoxyethylene nonyl phenyl | 13.0 |
| Polyoxyethylene sorbitan monolaurate | 13.3 |
| Polyoxyethylene sorbitol lanolin | 14.0 |
| Polyoxyethylene stearyl alcohol | 15.3 |
| Polyoxyethylene 20 cetyl ether | 15.7 |
| Polyoxyethylene 40 stearate | 16.9 |
| Polyoxyethylene monostearate | 17.9 |
| Sodium oleate | 18.0 |
| Potassium oleate | 20.0 |

The osmotically active core composition mass (3) of FIG. 1, is typically in the form of a solid conventional tablet, pellet, or multiparticulate. The core is completely encased by the controlled porosity wall (2). The core can be comprised of either a pure agent (4) or a mixture of agents (4, 5, etc.) combined to give the desired manufacturing and ultimate agent(s) delivery characteristics. The number of agents that may be combined to make the core is substantially without an upper limit with the lower limit equaling one component. The preferred specifications for the core are summarized below and include:

| 1. | Core Loading (size) | 0.05 nanograms to 5 grams or more (includes dosage forms for humans and animals) |
| --- | --- | --- |
| 2. | Osmotic pressure developed by a solution of the core | 8 to 500 atmospheres, typically, with commonly encountered water soluble drugs and excipients; however osmotic pressures greater than zero are within guidelines |
| 3. | Core solubility | to get continuous, uniform release (zero-order kinetics) of 90% or greater of the initially loaded core mass, the ratio of the core mass solubility, S, to the core mass density, $\rho$, that is S/$\rho$, must be 0.1 or lower. Typically this occurs when 10% of the initially loaded core mass saturates a volume of external fluid equal to the total volume of the initial core mass. |

S/$\rho$ ratios greater than 0.1 fall within the workings of the invention and result in lower percentages of initial core mass delivered under zero-order kinetics. S/$\rho$ can be selected to give acceptable combined characteristics of stability, release rate, and manufacturability.

In cases where the active agent has the desired solubility, osmotic pressure, density, stability, and manufacturability characteristics, there is no critical upper limit as to the amount that can be incorporated into a core mass and typically will follow the core loading (size)

specification 1. The lower limit ratio of agent to excipient is dictated by the desired osmotic activity of the core composition, the desired time span of release, and the pharmacological activity of the active agent. Generally the core will contain 0.01% to 90% by weight or higher, of an active agent in mixture with another solute(s). Representative of compositions of matter that can be released from the device and can function as a solute are, without limitation, those compositions soluble in fluids inside the core compartment as described. The solubilized constituents create a water activity gradient across the wall, (2), of FIG. 1, resulting in osmotically actuated fluid movement constituting the osmotic pump action of the invention.

The expression "active agent" as used herein broadly includes any compound, or mixture thereof, that can be delivered from the system to produce a beneficial result. The agent can be soluble in fluid that enters the reservoir and functions as an osmotically effective solute or it can have limited solubility in the fluid and be mixed with an osmotically effective compound soluble in fluid that is delivered from the system. The active agent includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit that environment of use.

In the specification and the accompanying claims, the term "drug" includes any physiologically or pharmacologically active substances that produce a localized or systemic effect or effects in animals, which term includes mammals, humans and primates. The term also includes domestic household, sport or farm animals such as sheep, goats, cattle horses and pigs, for administering to laboratory animals such as mice, rats and guinea pigs, and to fishes, to avians, to reptiles and zoo animals. The term "physiologically" as used herein denotes the administration of drug to produce normal levels and functions. The term "pharmacologically" denotes variations in response to amounts of drug including therapeutics. *Stedman's Medical Dictionary,* 1966, published bY Williams & Wilkins, Baltimore, Md. The phrase drug formulation as used herein means the drug is in the compartment by itself, or the drug is in the compartment mixed with an osmotic solute, binder, dye, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autocoid systems, alimentary and excretory systems, inhibitory of autocoids and histamine systems, those materials that act on the central nervous system such as hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and α-bromoisovaleryl urea; hypnotic and sedative urethanes and disulfanes; psychic energizers such as isocoboxazid, nialamide, phenelzine, imipramine, amitryptyline hydrochloride, tranylcypromine and pargylene; and protryptyline hydrochloride, tranquilizers such as chloropromazine, promazine, fluphenzaine, reserpine, deserpidine, meprobamate, and benzodiazepines such as chlordiazepoxide; anticonvulsants such as primidone, enitabas, diphenylhydantion, ethyltion, pheneturide and ethosuximide; muscle relaxants and antiparkinson agents such as mephenesin, methocarbomal, cyclobenzaprine trihexylphenidyl, levodopa/carbidopa, and biperiden; antihypertensives such as α-methyldopa and L-β-3-4-dihydroxyphenylalanine, and pivaloyloxyethyl ester of α-methyldopa hydrochloride dihydrate; analgesics such as morphine, codeine, meperidine, nalorphine; antipyretics and anti-inflammatory agents such as aspirin, indomethacin, sodium indomethacin trihydrate salicylamide, naproxen, colchicine, fenoprofen, sulindac, diflunisal, diclofenac, indoprofen and sodium salicylamide; local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as $PGE_1$, $PGE_2$, $PGF_{1\alpha}$, $PGF_{2\alpha}$ and PGA; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-aminoquinolines and pyrimethamine; hormonal agents such as dexamethasone prednisolone, cortisone, cortisol and triamcinolone; androgenic steroids such as methyltestosterone, and fluoxmesterone; estrogenic steroids such as 17β-estradiol, α-estradiol, estriol, α-estradiol 3-benzoate, and 17-ethynyl estradiol-3-methyl ether; progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-(5(10)-estren-3-one, and 9β,10α-pregna-4,6-diene-3,20-dione; sympathomimetic drugs such as epinephrine, phenylpropoudamine hydrochloride, amphetamine, ephedrine and norepinephrine; hypotensive drugs such as hydralazine; cardiovascular drugs such as procainamide, procainamide hydrochloride, amyl nitrite, nitroglycerin, dipyredamole, sodium nitrate and mannitol nitrate; diuretics such as chlorathiazide, acetazolamide, methazolamide, hydrochlorothiazide, amiloride hydrochloride and flumethiazide, ethacrynic acid, furosemide; antiparasitics such as bephenium, hydroxynaphthoate, dichlorophen and dapsone; and neoplastics such as mechlorethamine, uracil mustard, 5-fluorouracil, 6-thioguanine and procarbazine; β-blockers such as pindolol, propranolol, practolol, metoprolol, oxprenolol, timolol, timolol maleate, atenolol, alprenolol, and acebutolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin $B_{12}$; essential amino acids; essential fats; eye drugs such as timolol, timolomaleate, pilocarpine, pilocarpine salts such as pilocarpine nitrate, pilocarpine hydrochloride, dichlorphenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate; and drugs that act on α-adrenergic receptors such as clonidine hydrochloride.

Additional preferred drugs include quinoline and naphthyridine carboxylic acids and related compounds, such as 1-ethyl-6-fluoro-1,4-dihydro-4-oxo-7-(1-piperazinyl)-3-quinolinecarboxylic acid; 1-ethyl-1,4-dihydro-7-methyl-4-oxo-1,8-naphthyridine-3-carboxylic acid; 5-ethyl-5,8-dihydro-8-oxo-1,3-dioxolo-[4,5-g]quinoline-7-carboxylic acid; 8-ethyl-5,8-dihydro-5-oxo-2-(1-piperazinyl)pyrido[2,3-d]pyrimidine-6-carboxylic acid; 9-fluoro-6,7-dihydro-5-methyl-1-oxo-1H,5H-benzo[ij]quinoxolizine-2-carboxylic acid; 1-ethyl-1,4-dihydro-4-oxo-7-(4-pyridinyl)-3-quinolinecarboxylic acid; 1-ethyl-1,4-dihydro-4-oxo-[1,3]diox-olo[4,5-g]cinnoline-3-carboxylic acid; 9-fluoro-3-methyl-10-(4-methyl-1-piperazinyl)-7-oxo-2,3-dihydro-7H-pyrido[1,2,3-de][1,4]benzoxazine-6-carboxylic acid; 1-ethyl-6-fluoro-1,4-dihydro-7-(4-methyl-1-piperazinyl)-4-oxo-1,8-naphthyridine-3-carboxylic acid; 1-ethyl-6-fluoro-1,4-dihydro-7-(1-piperazinyl)-4-oxo-1,8-naphthyridine-3-carboxylic acid; 1-cyclopropane-6-fluoro-1,4-dihydro-4-oxo-7-(1-piperazinyl)-3-quinolinecarboxylic acid; 1-methylamino-6-fluoro-1,4-dihydro-4-oxo-7-(4-methyl-1-piperazinyl)-3-quinolinecarboxylic acid; 1-(4-fluoro-1-phenyl)-6-fluoro-1,4-dihydro-4-oxo-7-(1-piperazinyl)-3-quinolinecarboxylic acid; 1-(4-fluoro-1-phenyl)-6-fluoro-1,4-dihydro-4-oxo-7-(4-methyl-1-piperazinyl)-3-quinolinecarboxylic acid; 1-(4-fluoro-1-phenyl)-6-fluoro-1,4-dihydro-4-oxo-7-(1-piperazinyl)-1,8-naphthyridine-3-carboxylic acid; and 1-ethyl-6-fluoro-1,4-Dihydro-4-oxo-7-(3-ethylaminomethyl-1-pyrrolidinyl)-8-fluoro-3-quinolinecarboxylic acid.

Additional preferred drugs include drugs which affect the respiratory tract such as budesonide, enprofylline, tranilast, albuterol, theophylline, aminophylline, brompheniramine, chlorpheniramine, promethazine, diphenhydramine, azatadine, cyproheptadine, terbutaline, metaproterenol, and isoproterenol; drugs which are antidepressants such as amiflamine, alaproclate, doxepin, trazedone, maprotiline, zimelidine, fluvoxamine; antipsychotic drugs such as haloperidol, thioridazine, trifluoperazine, MK-0212, and remoxipride; sedative hypnotic and antianxiety drugs such as triazolam, temazepam, chlorazepate, alprazolam, diazepam, flurazepam, lorazepam, oxazepam, hydroxyzine, prazepam, meprobamate, butalbital, and chlorzoxazone; antiparkinson drugs such as benztropine and L-647,339; hormonal and steroidal drugs such as conjugated estrogens, diethylstilbesterol, hydroxy progesterone, medroxy progesterone, norethindrone, betamethasone, methylprednisolone, prednisone, thyroid hormone, levothyroxine and MK-0621; antihypertensive and cardiovascular drugs such as isosorbide dinitrate, digoxin, nadolol, disopyramide, nifedipine, quinidine, lidocaine, diltiazam, verapamil, prazosin, captopril, enalapril, lisinopril, metyrosine, felodipine, tocainide, mexiletine, mecamylamine, and metyrosine; diuretic drugs such as spironolactone, chlorthalidone, metolazone, triamterene, methyclothiazide, and indacrinone; antiinflammatory drugs such as ibuprofen, phenylbutazone, tolmetin, piroxicam, melclofenamate, auranofin, flurbiprofen and penicillamine; analgesic drugs such as acetaminophen, oxycodone, hydrocodone, and propoxyphene; antiinfective drugs such as cefoxitin, cefazolin, cefotaxime, cephalexin, nicarbazin, amprolium, ampicillin, amoxicillin, cefaclor, erythromycin, nitrofurantoin, minocyline, doxycycline, cefadroxil, miconazole clotrimazole, phenazopyridine, clorsulon, fludalanine, pentizidone, cilastin, phosphonomycin, imipenem, arprinocid, and foscarnet; gastrointestinal drugs such as bethanechol, clidinium, dicyclomine, meclizine, prochlorperizine, trimethobenzamide, loperamide, ranitidine, diphenoxylate, famotidine, metoclopramide and omeprazole; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim and mevinolin.

The above list of drugs is not meant to be exhaustive. Many other drugs will certainly work in the osmotic pump of the instant invention.

Examples of beneficial drugs are disclosed in *Remington's Pharmaceutical Sciences*, 16th Ed., 1980, published by Mack Publishing Co., Easton, Penna.; and in *The Pharmacological Basis of Therapeutics*, by Goodman and Gilman, 6th Ed., 1980, Published by The MacMillian Company, London.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for examPle quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of active agent or active agent admixed with other osmotically active solutes present in the device is initially in excess of the amount that can be dissolved in the fluid that enters the reservoir. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the device can house from 0.05 ng to 5 grams or more, with individual devices containing, for example, 25 ng, 1 mg, 5 mg, 250 mg, 500 mg, 1.5 g and the like.

Mixtures of drug agent(s) with other osmotically effective compounds may be used to attract fluid into the device producing a solution of compound which is delivered from the device concomitantly transporting drug agent to the exterior of the device. Examples include magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phosphate, calcium lactate, d- mannitol, urea, inositol, sorbitol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37° C., in water, is listed in Table 2. In the table, the osmotic pressure $\pi$, is in atmospheres, atm. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 2, osmotic pressures of from 20 atm to 500 atm are set forth; of course, the invention includes the use of lower osmotic pressures from greater than zero, and higher osmotic pressures than those set forth by way of example in Table 2. For example, in the gastrointestinal tract, the osmotic pressure gradient across the wall in the compartment will be from greater than 0 up to 500 atm per membrane thickness. That is, the osmotic pressure in the compartment will be typically in excess of 8 atm up to 500 atm.

TABLE 2

| COMPOUND OR MIXTURE | OSMOTIC PRESSURE (atm) |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 335 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

The resulting device will have a water permeability driven by a saturated solution of the active agent, or mixtures of active agents with other osmotically active solutes, at the temperature of use, of 0.01 ml per cm$^2$ of surface area per day to 10 ml per cm$^2$ of surface area per hour.

EXAMPLE 1

A plurality of osmotic systems for the osmotically controlled release of the beneficial drug potassium chloride were made as follows: First, 650 mg aliquots of commercially-available reagent grade potassium chloride (active agent) were compressed to a hardness of 15Kg by standard compression techniques in a Stokes tableting machine fitted with a ⅜ inch extra deep concave punch. A total of 700 g of such tablets were prepared as osmotic core composition masses of the invention. Next, 36 g of Eastman cellulose acetate 398-10 (polymer) were added to methylene chloride (solvent), with subsequent addition of methanol (solvent) with high speed mechanical stirring to complete the dissolution of the polymer. To this was added 7.9 g of polyethylene glycol 400 (plasticizer, liquid pore forming additive and flux regulator). To this solution was added in dropwise fashion with stirring a second solution of water and methanol (solvent) containing 18 g of dissolved sorbitol (solid pore forming additive), to constitute the solution utilized to form the controlled porosity wall of the invention. The final solution contained approximately 2%, by weight, polymer in a solvent system of methylene chloride, methanol, and water in the approximate weight ratio of 15:10:1. The fluid permeability of the wall was $2.28 \times 10^{-15}$ cm$^3$ sec/g and its reflection coefficient was measured at $8.66 \times 10^{-4}$. Next, 700 g of the potassium chloride osmotic core tablets was charged into a commercial Uni-Glatt fluidized bed machine wherein the wall forming solution was applied to the cores until a thickness of 0.016 cm was attained. The finished osmotic systems were dried in an oven at 50° C. to facilitate removal of residual solvents.

Figure 2:
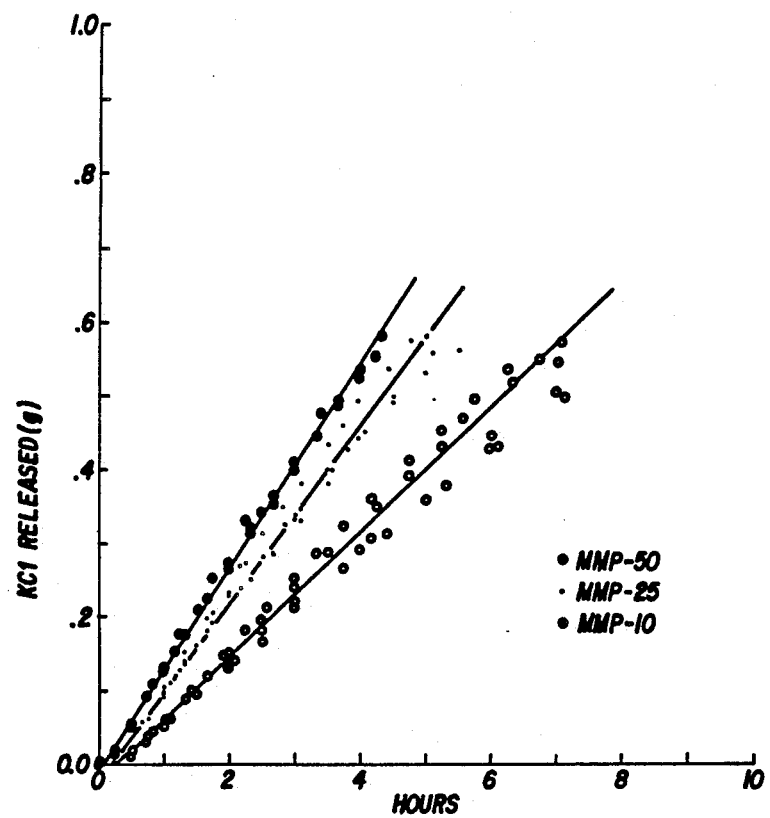
FIG. 2 is the release profile (statistical average of several pumps) of the pumps produced in Examples 1 through 3.
Figure 4:
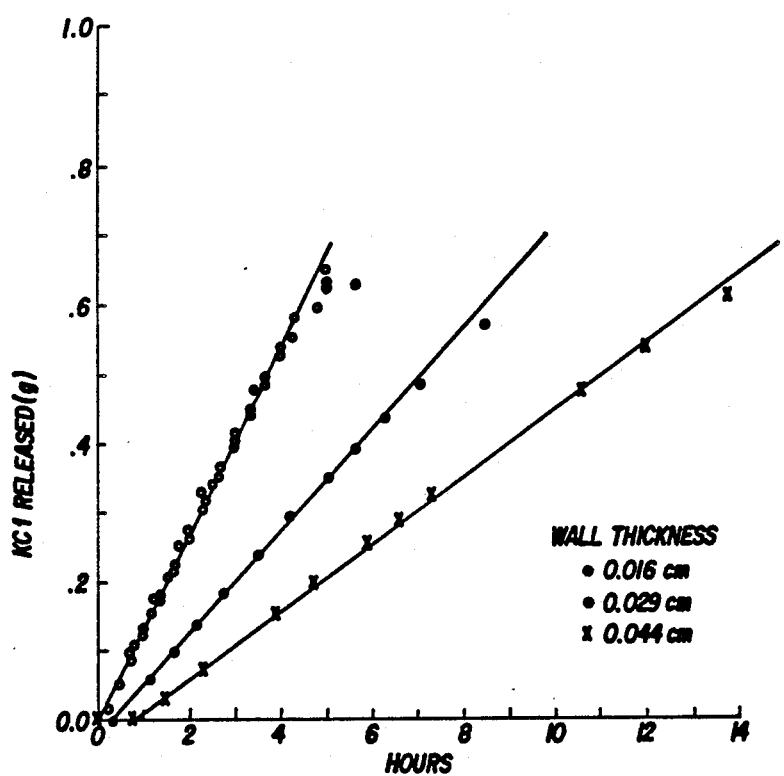

Finally, the potassium chloride release from these osmotic systems into distilled water was monitored conductiometrically at 37° C. in a commercial Applied Analytical standard dissolution apparatus Providing 100 rpm stirring. The release profile is dePicted in FIG. 2 labelled as MMP-50 (modified microporous, sorbitol 50% of polymer wt) and was found to be continuous at a mean rate of 139 mg per hour for a prolonged period of approximately 4 hours. Since the solute is passing through the wall, it has a reflection coefficient substantially less than 1 and was determined to be less than 0.1. The amount of potassium chloride released with zero-order kinetics was consistent with the theoretically anticipated amount which was calculated with Equation 1 to be 82.7% of the initial KCl loaded into the core mass $$100 \times \frac{M_z}{M_t} = \left(1 - \frac{S}{\rho}\right) \times 100 \quad \text{(Eq. 1)}$$

where $M_z$ is the amount released in zero-order fashion, $M_t$ is the initial KCl load, S is the KCl solubility (343 g/ml), and $\rho$ is the density of solid KCl (2 g/cm$^3$).

EXAMPLE 2

A plurality of osmotic systems were manufactured according to the procedure of Example 1, wherein the conditions were as described except that the sorbitol content of the wall forming solution was 9 g. Potassium chloride release from these systems was monitored according to the procedure of Example 1. The release profile is depicted in FIG. 2 labelled as MMP-25 and was found to be continuous for a prolonged period at a mean rate of 120 mg per hour for approximately 5 hours. The fluid permeability of the wall was $1.69 \times 10^{-15}$ cm$^3$ sec/g and the reflection coefficient of the wall was less than 0.1.

EXAMPLE 3

A plurality of osmotic systems were manufactured according to the procedure of Example 1, wherein the conditions were as described except that the sorbitol content of the wall forming solution was 3.6 g. Potassium chloride release from these systems was monitored according to the procedure of Example 1. The release profile is depicted in FIG. 2 labelled as MMP-10 and was found to be continuous for a prolonged period at a mean rate of 80 mg per hour for approximately 7.5 hours. The fluid permeability of the wall was $0.81 \times 10^{-15}$ cm$^3$ sec/g and the reflection coefficient of the wall was less than 0.1.

EXAMPLE 4

A plurality of osmotic systems were manufactured according to the procedures of Example 1. Potassium chloride release from these systems was monitored conductiometrically at 37° C. in a commercial Applied Analytical standard dissolution apparatus under the various conditions of stirring: (a) 100 rpm continuously; (b) 100 rpm intermittent with 0 rpm; (c) and 0 rpm continuously. The potassium chloride release profiles of FIG. 3 kept their uniformity and configuration for a prolonged period without stirring induced effects for osmotic systems MMP-10, MMP-25, and MMP-50.

EXAMPLE 5

A plurality of osmotic systems were manufactured according to the procedure of Example 1, wherein the conditions were as described except that the wall forming solution was applied for sufficient duration so as to produce osmotic systems with wall thicknesses of 0.016 cm, 0.029 cm, and 0.044 cm. Potassium chloride release from these osmotic systems was monitored according to the procedure of Example 1. The release profiles depicted in FIG. 4 were continuous for a prolonged period with release rates decreasing with increasing wall thickness. A plot of 1/(wall thickness) versus mean release rate is given in FIG. 5 indicating that the osmotic release of potassium chloride is in accordance with the inverse proportionality:

$$\frac{\text{release}}{\text{rate}} \propto \frac{1}{\text{wall thickness}}$$

EXAMPLE 6

A plurality of osmotic systems were manufactured according to the procedure of Example 1, wherein the conditions were as described. Release of potassium chloride from these osmotic systems into 200 ml volumes of unstirred water, pH 1.2 HCl buffer, or pH 8 phosphate buffer solutions adjusted with sodium chloride to be isoosmotic with blood was followed by conductiometrically analyzing the potassium chloride residue from 3 osmotic systems at each time interval by cutting the wall and dissolving the contents in distilled water. Based on an initial amount of 0.65 g KCl in the core composition, the amount of KCl released at each time was calculated with equation 2.

$$(.65 \text{ g}) - \frac{\text{osmotic (system) residue KCl (g)}}{} = \text{g KCl released} \quad \text{(Eq. 2)}$$

Figure 6:
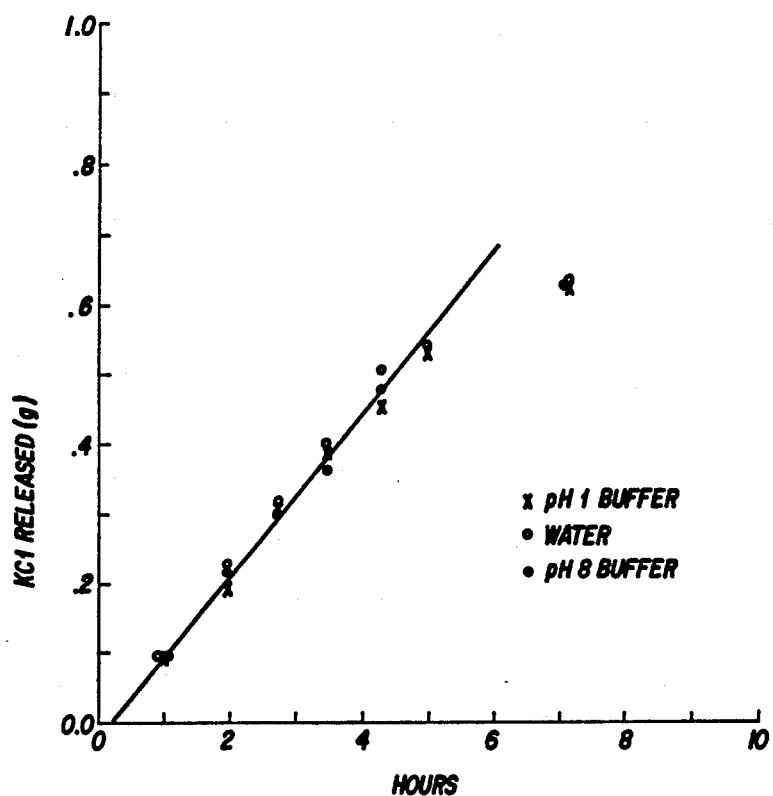

The release profile is depicted in FIG. 6 where a clear independence of release rate from the pH of the external fluid is evident.

EXAMPLE 7

Figure 7:
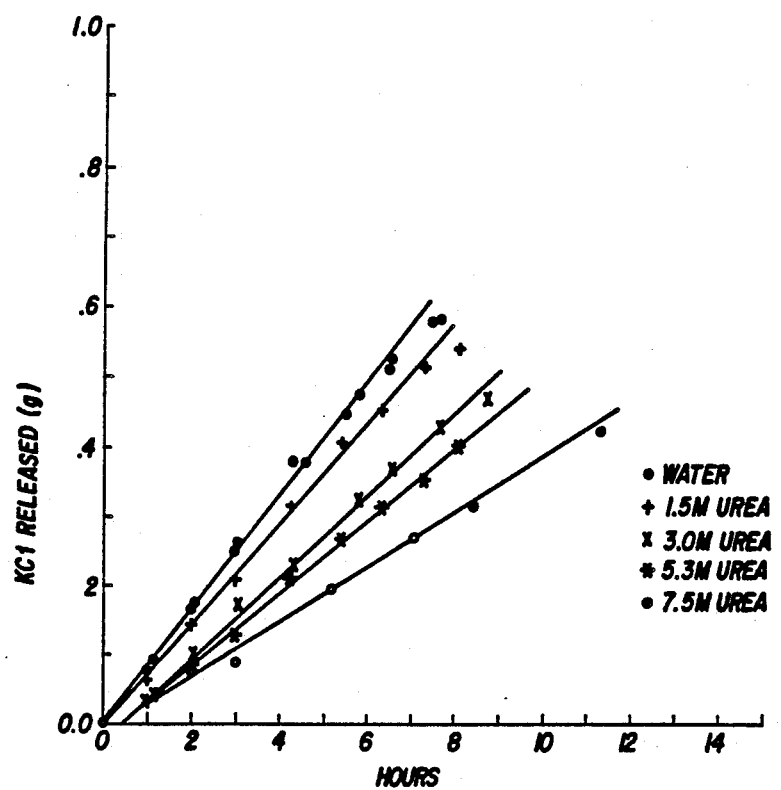

A plurality of osmotic systems were manufactured according to the procedure of Example 1, wherein the conditions were as described. Release of potassium chloride from these osmotic systems into 200 ml volumes of unstirred distilled water, 1.5 molar urea, 3 molar urea, 5.3 molar urea, or 7.5 molar urea at 25° C. was followed by conduction-metrically analyzing the potassium chloride residue from 3 osmotic systems at each time interval by cutting the wall and dissolving the core composition contents in distilled water. The release profiles are depicted in FIG. 7 where increasing the urea concentration in the external fluid reduced the release rate of the potassium chloride from the osmotic system as evidenced by the diminishing slopes of the lines.

The osmotic pressures of the various fluids of concern were calculated using established thermodynamic relationships and experimental data as given in *Electrolyte Solutions 2nd Revised Edition*, by R. A. Robinson and R. H. Stokes, pages 29–30, 1959, published by Butterworth and Co. Ltd., London; *Aust. J. Chem.*, Vol. 20, pages 2087–2100; and *J. Amer. Chem. Soc.*, Vol. 60, pages 3061–3070. The net osmotic pressure difference that exists across the wall of the osmotic system was calculated with Equation 3.

$$\pi_{net} = \pi_{\substack{saturated \\ KCl \text{ in } H_2O}} - \pi_{\substack{urea \\ in\ H_2O}} \quad \text{(Eq. 3)}$$

A plot of potassium chloride release rate versus $\pi_{net}$ is given in FIG. 8 to illustrate the dependence of core composition release rate on the osmotic pressure difference across a wall barrier permeable to both an external fluid and core composition.

EXAMPLE 8

A plurality of osmotic systems for the osmotically-controlled release of the beneficial drug sodium indomethacin trihydrate were made as follows: First, 3 g sodium indomethacin trihydrate were mixed with 4.5 g sorbitol in a commercial Mini Mill for 1 minute. 250 mg aliquots were individually weighed and compressed in a standard $\frac{3}{8}$ inch extra deep concave tableting die under 3 tons pressure on a Carver hydraulic press to form the core composition masses of the invention. 30 Such core masses were manufactured. The solution utilized to form the controlled porosity wall was prepared according to the procedure of Example 1, wherein the conditions were as described, except that the sorbitol content of the wall forming solution was 9 g. Next, 30 core composition masses were mixed with 700 g of potassium chloride placebo tablets in a commercial Uni-Glatt fluidized bed machine, wherein the wall forming solution was applied to the core masses until a thickness of 95 microns was attained. The finished osmotic systems were dried in an oven to 50° C. to facilitate removal of residual solvents.

Figure 9:
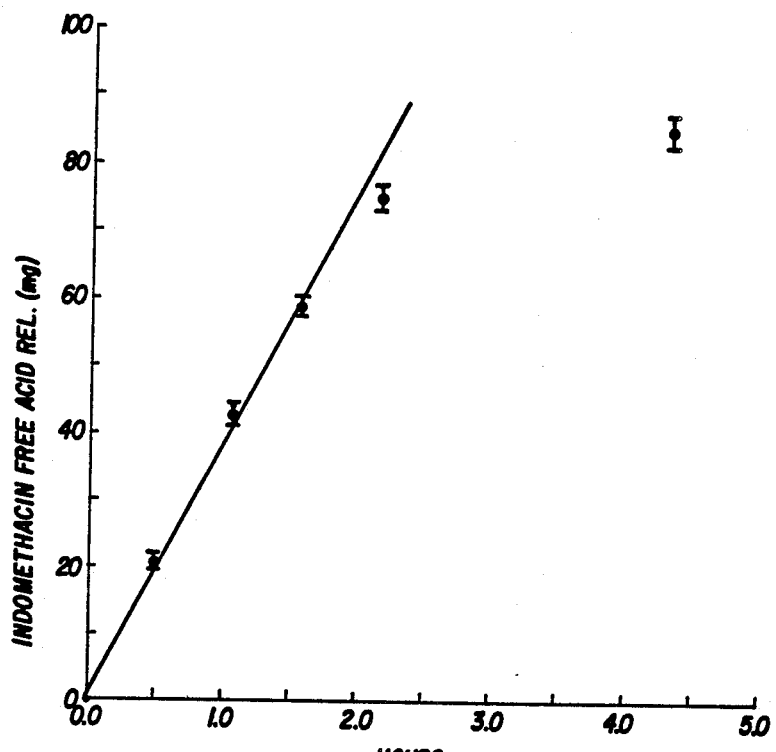

The release of sodium indomethacin from these osmotic systems into 0.07M phosphate buffer, pH 6.6, was monitored by ultraviolet light absorption measurements at a wavelength of 320 nm in standard 1 cm pathlength quartz cells in a commercial double beam Beckman Acta V spectrophotometer. Release was conducted at 37° C with 100 rpm stirring provided by paddles in a commercial Applied Analytical standard dissolution apparatus. The release profile is depicted in FIG. 9 where the equivalent mgs of indomethacin in free acid form released versus time in hours is plotted. The release was continuous and uniform for a prolonged period at a mean rate of 34.6 mg/hr.

EXAMPLE 9

A plurality of osmotic systems for the osmotically-controlled release of the beneficial drug sodium indomethacin trihydrate were made as follows: First, 3 g sodium indomethacin trihydrate was mixed with 13.5 g sorbitol in a commercial Mini-Mill for 1 minute. 550 Mg aliquots were individually weighed and compressed in a standard ⅜ inch extra deep concave tableting die under 3 tons pressure on a Carver hydraulic press to from the core composition masses of the invention. 30 Such core masses were manufactured. The wall forming solution was prepared according to the procedure of Example 8, wherein the conditions are as described except that the sorbitol content of the wall forming solution was 3.6 g. Next, 30 core composition masses were mixed with 700 g of potassium chloride placebo tablets in a commercial Uni-Glatt fluidized bed machine, wherein the wall forming solution was applied to the core masses until a thickness of 130 microns was attained. The finished osmotic systems were dried in an oven at 50° C. to facilitate removal of residual solvents.

Figure 10:
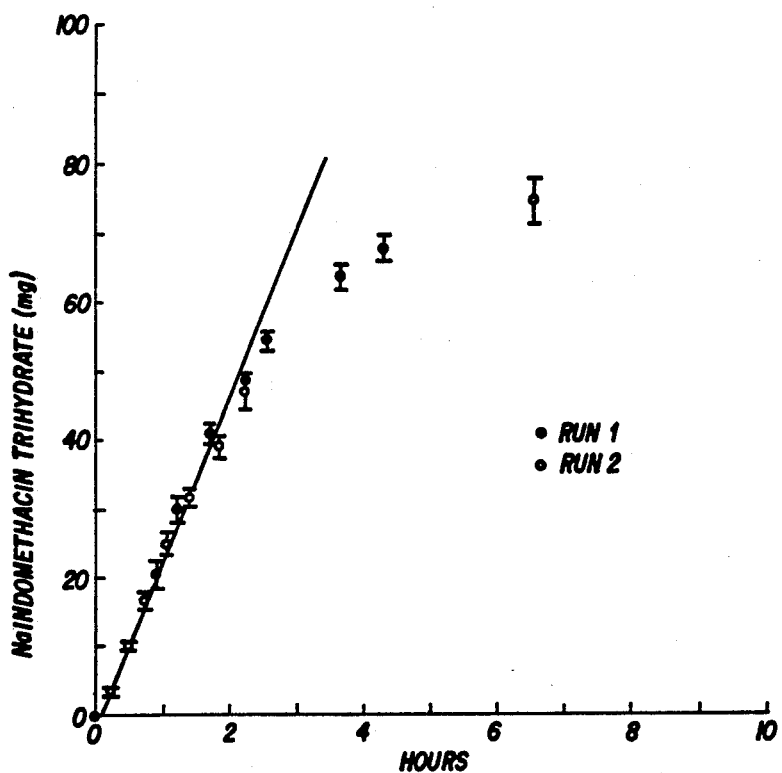

The release of sodium indomethacin from these osmotic systems into 0.07M phosphate buffer, pH 7.4, made isoosmotic to blood with additional sodium chloride was monitored by ultraviolet light absorption measurements at a wavelength of 320 nm in standard 1 cm pathlength quartz cells in a commercial Beckman DU-7U spectrophotometer. Release was conducted at 37° C. with 100 rpm stirring provided by paddles in a commercial Applied Analytical dissolution apparatus. The release profile is depicted in FIG. 10 where the mgs of sodium indomethacin trihydrate released versus time in hours is plotted. The release was continuous and uniform for a prolonged period at a mean rate of 20.7 mg/hr of sodium indomethacin trihydrate.

EXAMPLE 10

A plurality of osmotic systems for the osmotically controlled release of the beneficial drug cyclobenzaprine HCl were made as follows: First, 3.7 g cyclobenzaprine HCl were mixed with 60 g α-D-glucose and 17.5 g distilled water to form a mass that was forced through a No. 12 screen and dried in vacuo at 50° C. for 24 hours to constitute granules for direct compression. Aliquots containing 29 mg cyclobenzaprine HCl were individually weighed and compressed in a standard 7/16 inch tableting die under 4 tons pressure to form core composition masses of the invention. 14 Such masses were manufactured. The wall forming solution was prepared according to the procedure of Example 8, wherein the conditions were as described. Next, 14 core composition masses were mixed with 700 g of potassium chloride placebo tablets in a commercial Uni-Glatt fluidized bed machine, wherein the wall forming solution was applied to the core masses until a thickness of 110 microns was attained.

Figure 11:
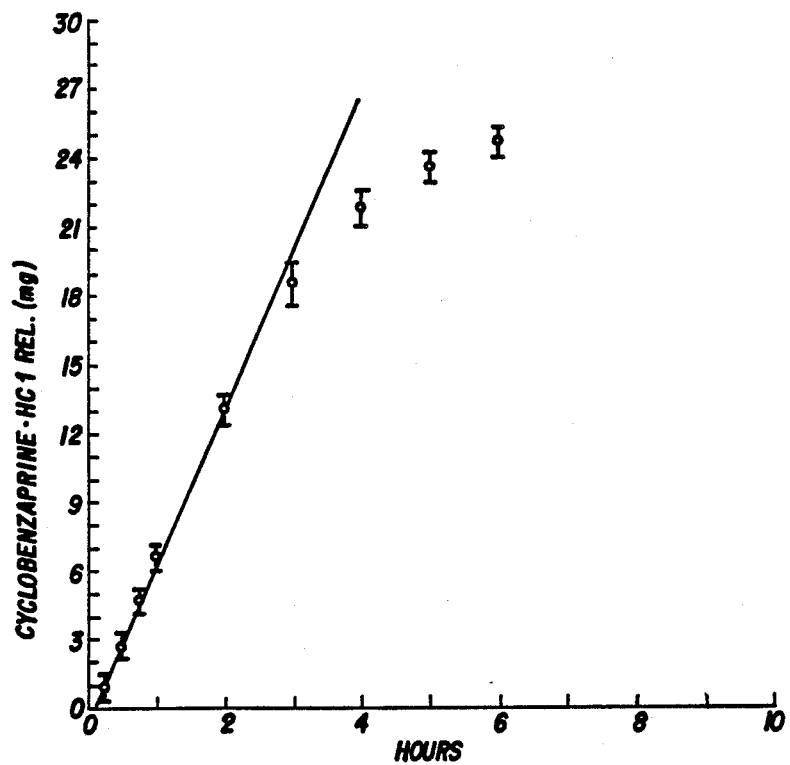

The release of cyclobenzaprine HCl from these osmotic systems into distilled water was monitored by ultraviolet light absorption measurements at a wavelength of 290 nm in standard 1 cm pathlength quartz cells in a commercial Beckman DU-7U spectrophotometer. Release was conducted at 37° C. with 100 rpm stirring provided by paddles in a commercial Applied Analytical standard dissolution apparatus. The release profile is depicted in FIG. 11 where the mgs of cyclobenzaprine HCl released was continuous and uniform for a prolonged period at a mean rate of 6.9 mg/hr.

The total amount released in a zero-order fashion was approximately 18 mg which agrees well with the theoretically anticipated amount based on the solubility and density of the major osmotic agent in the core composition as calculated from Equation 4:

$$\begin{array}{l}\text{fraction released} \\ \text{in zero-order} \\ \text{fashion}\end{array} = 1 - \frac{\text{solubility of dominant osmotic agent}}{\text{density of the solid dominant osmotic agent}} \quad \text{(Eq. 4)}$$

In this example glucose was the major osmotic agent with a solubility to density ratio of 0.38 that calculates to 17.9 mg cyclobenzaprine HCl released in zero-order fashion.

EXAMPLE 11

A plurality of osmotic systems for the osmotically controlled release of the beneficial drug cyclobenzaprine HCl were made according to the Procedure of Example 10, wherein the conditions were as described except that the core masses contain 25 mgs cyclobenzaprine HCl and the wall applied to a final thickness of 260 microns.

Figure 12:
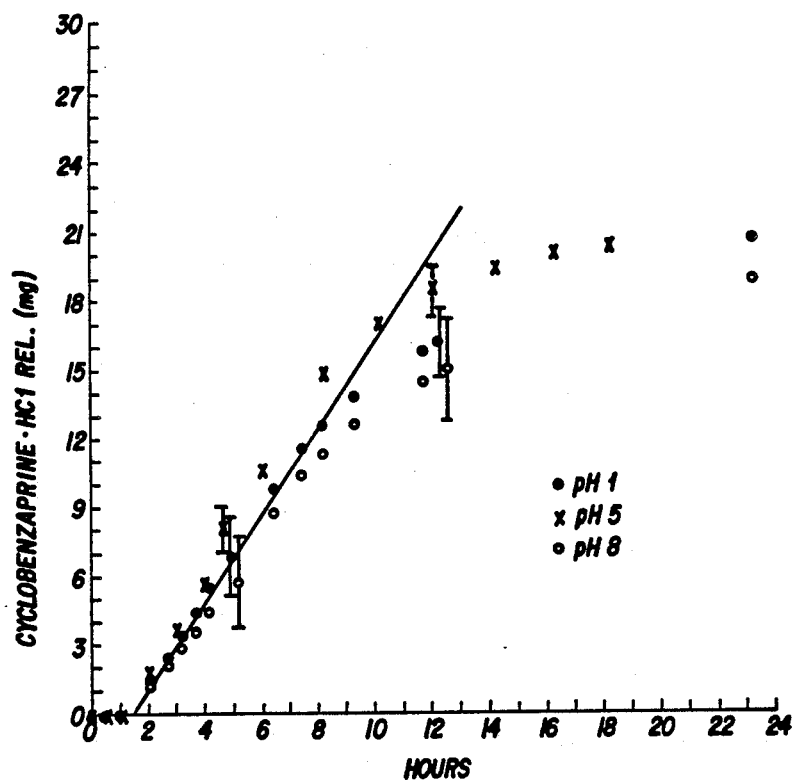

The release of cyclobenzaprine HCl from these osmotic systems into 0.07M phosphate buffers, pH 5 and pH 8, and HCl buffer pH 1 was monitored by ultraviolet light absorption measurements at a wavelength of 290 nm in standard 1 cm pathlength quartz cells in a commercial Beckman DU-7U spectrophotometer. Release was conducted at 37° C. with 100 rpm stirring provided by paddles in a commercial Applied Analytical dissolution apparatus. The release profiles are depicted in FIG. 12 where cyclobenzaprine HCl release was uniform and continuous at all pH's examined for a prolonged Period with zero-order release kinetics observed for delivery of 15.5 mgs which is the theoretically anticipated value based on the solubility and density of the major osmotic agent, glucose. The mean release rates at pH 1, pH 5, and pH 8 were 1.80 mg/hr, 2.14 mg/hr, and 1.65 mg/hr respectively.

Cyclobenzaprine HCl has a pKa of about 8.5 and would be anticipated to have a reduction in solubility as the pH increases. Analysis of fluid within the core of osmotic systems indicated that the pH within the core was not the same as the pH in the external fluid, and that cyclobenzaprine HCl was present in a dissolved state within the core fluids. The observed insensitivity of cyclobenzaprine HCl release to external fluid pH suggests that the intrinsic solubility of cyclobenzaprine is not exceeded in the examples given and the release rate is determined principally by the solubility behavior of the glucose component in the core.

EXAMPLE 12

A plurality of osmotic systems for the osmotically-controlled release of the beneficial drug potassium chloride were made as follows: First, 0.78 g aliquots of potassium chloride were compressed to a hardness of 15 kg by standard compression techniques in a Stokes tableting machine fitted with a ⅜ inch extra deep concave punch. A total of 2 kg of such tablets were prepared as osmotic core composition masses of the invention. Next, 50 g of commercial polymer Eudragit RS-100 were added to methylene chloride with subsequent addition of methanol and high speed mechanical stirring to complete the dissolution of the polymer. To this was added 11 g of polyethylene glycol 400. To this solution was added in dropwise fashion, with stirring, a second solution of water and methanol containing 12.5 g of sorbitol, to constitute the solution utilized to form the controlled porosity wall of the invention. The final solution contained approximately 2.5%, by weight polymer in a solvent system of methylene chloride, methanol and water in the approximate weight ratio of 15:10:1. Next, about 500 ml of the potassium chloride tablet core masses were charged into a commercial Freund Hi-Coater baffled pan coating machine wherein the wall forming solution was applied to the cores until a thickness of 120 microns was attained. Twenty-five of the tablets were removed at this point with the remainder coated to a final thickness of 190 microns.

Figure 13:
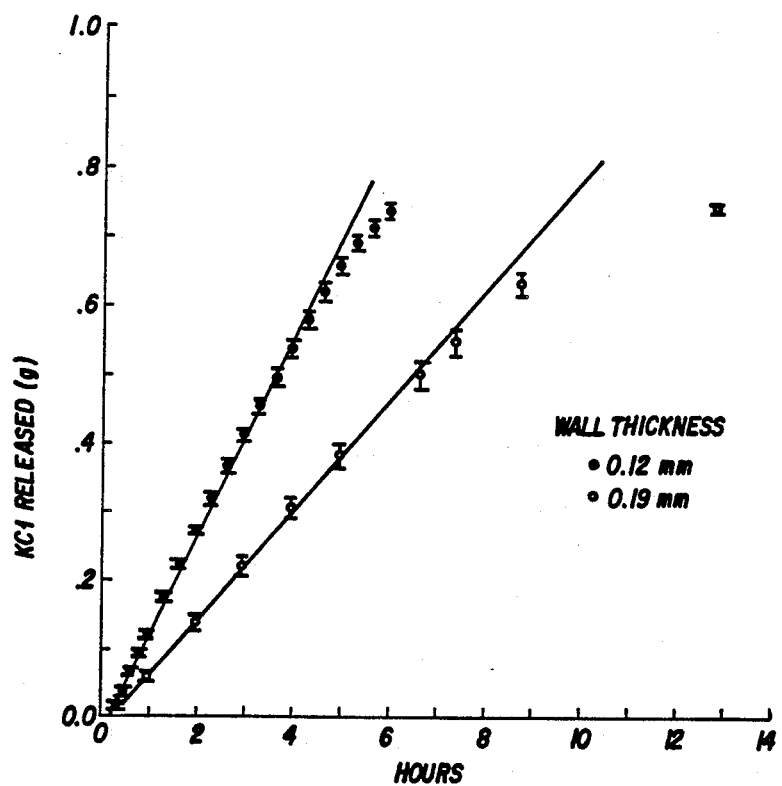

The release of potassium chloride from these osmotic systems into distilled water was monitored conductiometrically at 37° C. in a commercial Applied Analytical standard dissolution apparatus providing 100 rpm stirring. The release profiles are depicted in FIG. 13 and were continuous and uniform for prolonged periods and agreed with the theoretical predictions of Equation 1, Example 1. The mean release rates are 0.14 g/hr and 0.078 g/hr for the 120 micron and 190 micron wall thicknesses respectively with the rate inversely proportional to the wall thickness.

EXAMPLE 13

A plurality of osmotic systems for the osmotically-controlled release of the beneficial drug cyclobenzaprine HCl were made as follows: Core composition masses were manufactured according to the procedures of Example 9, wherein the conditions were as described except that the cyclobenzaprine HCl content of each core was 26 mg. Next, 37.5 g Eudragit RS 100 and 12.5 g Eudragit RL 100 (polymers) were added to methylene chloride (solvent) with subsequent addition of methanol (solvent) and high speed mechanical stirring to complete the dissolution of the polymer and give a polymer blend having a water permeability intermediate to that of the individual Eudragit components. To this solution was added in dropwise fashion, with stirring, a second solution of water and methanol containing 25 g of dissolved sorbitol, to constitute the solution utilized to form the controlled porosity wall of the invention. The final solution contained approximately 2.5%, by weight, polymer in a solvent system of methylene chloride, methanol and water in the approximate weight ratio of 15:10:1. Next, 30 core composition masses were mixed with 500 ml of placebo potassium chloride tablets in a commercial Freund Hi-Coater pan coating machine wherein the wall forming solution was applied to the cores until a thickness of 285 microns was attained.

Figure 14:
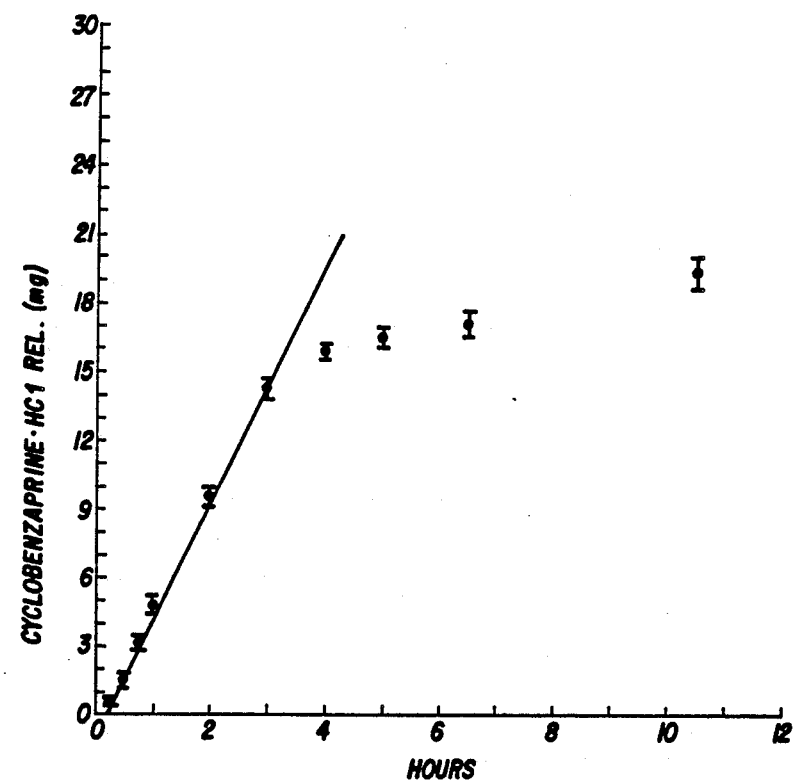

The release of cyclobenzaprine HCl from these osmotic systems into 0.07M .05 phosphate buffer, pH 7.4, made isoosmotic to blood with sodium chloride, was monitored by ultraviolet light absorption measurements at a wavelength of 290 nm in standard 1 cm pathlength quartz cells in a commercial Beckman DU-7U spectrophotometer. Release was conducted at 37° C. with 100 rpm stirring provided by Paddles in a commercial Applied Analytical dissolution apparatus. The release profile is depicted in FIG. 14 where cyclobenzaprine HCl release was uniform and continuous for a prolonged period with zero-order kinetics in effect for release of approximately 16 mg of drug which agreed closely with the theoretically anticipated amount of 16.1 mg calculated with Equation 4 of Example 10 with the major osmotic agent, glucose, dominating.

EXAMPLE 14

Multiparticulate osmotic systems for the controlled release of the beneficial drug potassium chloride were made as follows: First, 45 mg aliquots of commercial reagent grade potassium chloride were compressed by standard compression techniques in a Stokes tableting machine fitted with a ⅛ inch concave punch. A total of 1500 g of such particles were prepared as core masses of the invention. The wall forming solution was prepared according to the procedure of Example 1, wherein the conditions were as described except that the sorbitol content was 9 g. Next, 500 g of the core particles were charged into a commercial Uni-Glatt fluidized bed machine wherein the wall forming solution was applied to the cores until a thickness of 0.015 cm was attained. These particulate osmotic systems served as the multiparticulate components of the finished comPosition osmotic system. The particulate osmotic systems thus prepared were then utilized to deliver potassium chloride when administered as either a single particle, or a multiplicity of particles, to give the desired dose and rate of drug delivery. As a matter of convenience multiparticulates are commonly loaded into gelatin capsules for administration.

Figure 15:
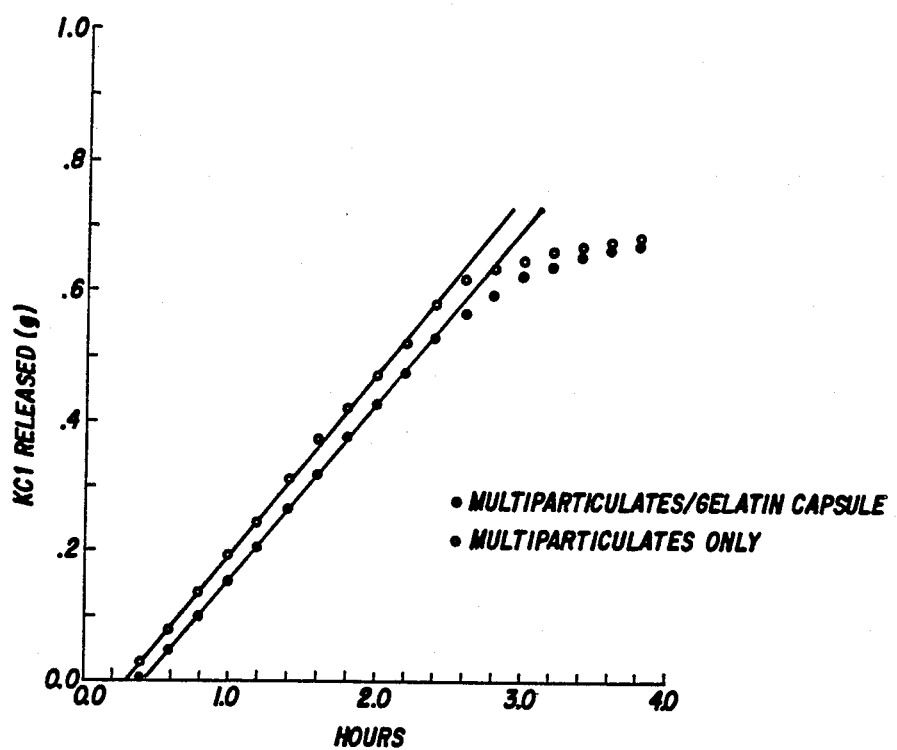
Figure 16:
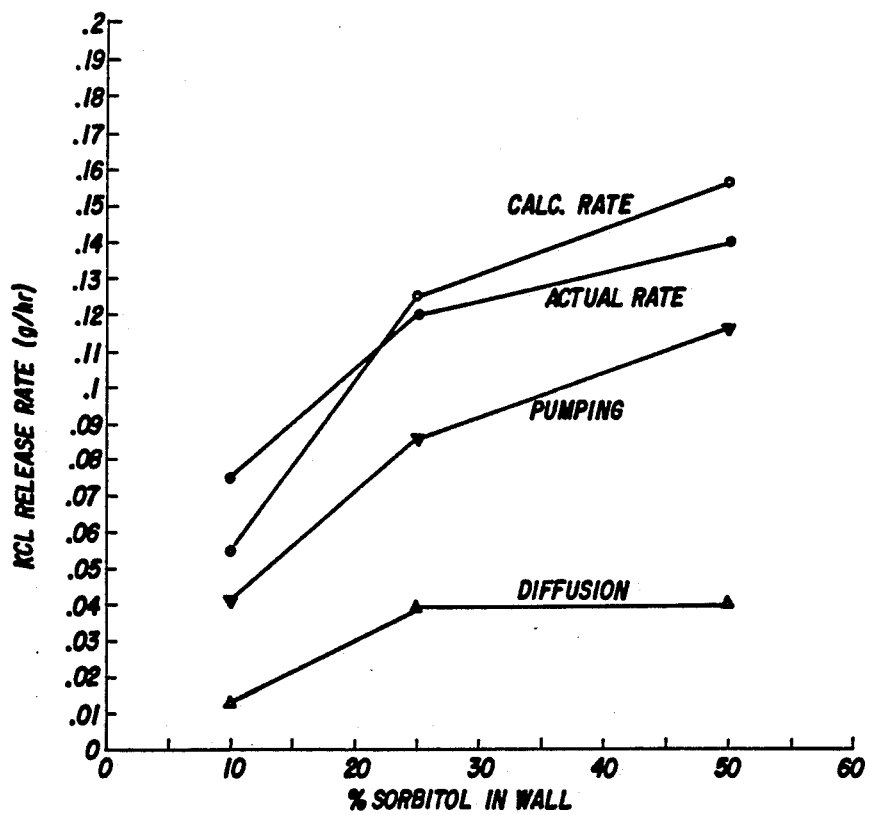

The release of potassium chloride from multiparticulate osmotic systems into 12 one liter aliquots of distilled water receptor media was monitored conductiometrically at 37° C. in a commercial VanKel standard dissolution apparatus providing 100 rpm stirring with paddles. Each of six receptor media were charged with 1 No. 00 gelatin capsule containing 15 particulate osmotic devices. The remaining 6 receptor media were charged with 15 particulate osmotic devices without the aid of a gelatin capsule. The release profiles are depicted in FIG. 15. The release rates with and without gelatin capsules were 0.274 g/hr and 0.278 g/hr respectively, which suggested the steady state release rate was independent of the gelatin capsule. The lag time was approximately 8 minutes longer with the gelatin capsule systems reflecting the time required for water to penetrate the gelatin before osmotic delivery of agent could begin. The theoretically anticipated release of 0.56 g of KCl with zero-order kinetics was observed. The release rates for these multiparticulate systems were within 7% of the release rates observed with a single large osmotic system having a similar wall (Example 2) when the rates were normalized for wall thickness and surface area differences. This indicated that the mechanism of osmotic delivery did not change with the size reduction to small particles.

EXAMPLE 15

Transmembrane flux of water was measured at 37° C. in a jacketed glass osmosis cell having two compartments of equal volume (185 ml) separated by a 14.34 cm$^2$ water equilibrated membrane sheet. Each compartment was stirred continuously at 600 rpm with internally driven magnetic stir bars positioned immediately adjacent to the membrane. Initially, one chamber was filled with deionized water. The second chamber was filled with a saturated aqueous solution of potassium chloride containing excess solid and fitted with a capillary tube 35 cm long with an 0.5 mm diameter core. The capillary was gravimetrically calibrated for volume using deionized water. The osmotically driven volume flux of water, dV/dt, from the first chamber into the second was measured by following the rise of fluid in the capillary with a cathetometer accurate to 0.01 cm. The diffusive flux of potassium chloride from the second chamber into the first chamber was measured conductiometrically under the same conditions as the water flux measurements except that the capillary was eliminated. Fluid levels in both chambers were kept equal throughout the diffusion experiments to eliminate hydrostatic pressure effects.

The membranes examined were identical in composition to walls applied to core tablets in Examples 1, 2 and 3 and were prepared by spraying onto a flat glass substrate. The measured volume flux of water, dV/dt, of Equation 1, for each membrane was multiplied by the potassium chloride solubility, $S=0.343$ g/cm$^3$, and normalized to a wall thickness of 0.016 cm and area of 2.67 cm$^2$ to correspond to the wall dimensions of the devices in Examples 1, 2 and 3. This was the calculated osmotic pump contribution to the total release.

The diffusive contribution, $(dM/dt)_D$, was measured directly and normalized to a wall thickness of 0.016 cm and area of 2.67 cm$^2$ The sum of the normalized osmotic pump and diffusive contributions was the calculated total release rate anticipated for devices similar to those of Examples 1, 2 and 3. These values were compared to the actual observed Performance of the devices in FIG. 16. The calculated rates agreed with the actual rates, with osmotic pumping the dominant contribution in all cases. The fractional contribution of osmotic pumping increased as the weight percentage of pore former in the films increased, while the diffusional contribution reached a constant value.

In all cases the walls were highly permeable to both water and salt. The agreement between the calculated rates and the actual rates indicated that the walls had a low level of selectivity between water and salt flux. The reflection coefficient, $\sigma$, is an established indicator of membrane selectivity and has been defined in *Biochimica et Biophysica Acta*, Vol. 27, page 236, such that $\sigma=0$ for a totally non-selective membrane and $\sigma=1$ for a totally selective membrane that is permeable to solvent (water) only. The low selectivity observed clearly indicated that $\sigma$ was less than one. The data of FIG. 16 were consistent with $\sigma$ values in the range 0 to 0.8. In fact, the $\sigma$ values for MMP-50 was determined to be $8.66 \times 10^{-4}$ and the $\sigma$ values from MMP-25 and MMP-10 estimated at less than 0.1.

EXAMPLE 16

Sections of the walls from devices described in Example 2 were equilibrated in deionized water for 8 hours to leach out the water soluble pore forming additives. These samples were critical point dried with carbon dioxide by standard methods and viewed with a scanning electron microscope. A typical micrograph is presented in FIG. 17. The walls were sponge-like in appearance with a distribution of pores that were less than 100 microns in diameter.

What is claimed is:

1. An osmotic pump, for the controlled release of a pharmaceutically active agent to an environment of use, said pump consisting essentially of:
   (A) a core comprises at least one pharmacologically active agent soluble in an external fluid, or a mixture of an agent having a limited solubility in the external fluid with an osmotically effective solute that is soluble in the fluid, which exhibit an osmotic pressure gradient across the wall against the external fluid surrounded by
   (B) a rate controlling water insoluble wall, having a fluid permeability of $6.96 \times 10^{-18}$ to $6.96 \times 10^{-14}$ cm$^3$ sec/g and a reflection coefficient of less than 0.5, prepared from:
   (i) a polymer permeable to water but impermeable to solute and
   (ii) 0.1 to 60% by weight, based on the total weight of (i) and (ii), of at least one pH insensitive pore forming additive dispersed throughout said wall.

2. The osmotic pump of claim 1, wherein said pore forming additive comprises:
   (a) 0.1 to 50%, by weight, solid additive, based on the total weight of (i) and (ii), and/or
   (b) 0.1 to 40%, by weight, liquid additive, based on the total weight of (i) and (ii), not to exceed a total weight % of pore forming additive of 60%.

3. The osmotic pump of claim 1, wherein said reflection coefficient is less than 0.1.

4. The osmotic pump of claim 1, further comprising:
   (C) 0 to 50 parts per 100 parts of (i) and (ii) of plasticizer and flux regulating additives and
   (D) 0 to 40 parts per 100 parts of (i) and (ii), of surfactant additive.

5. The osmotic pump of claim 1, wherein said water insoluble wall is 1 to 1,000 microns thick and wherein 5 to 95% of the resulting wall pores are between 10 angstroms and 100 microns in diameter.

6. The osmotic pump of claim 5 wherein said wall is 20 to 500 microns thick and said wall pores are between 10 angstroms and 25 microns in diameter.

7. The osmotic pump of claim 1, wherein at least 0.05 ng of active agent are used.

8. The osmotic pump of claim 7, wherein at least 1 microgram of active agent is used.

9. The osmotic pump of claim 1, wherein said polymer is selected from the group consisting of cellulose esters, acylated polysaccharides, polyurethane, polymers of acrylic and methacrylic acid and esters thereof, poly (ortho ester)s, polyacetals and mixtures thereof.

10. The osmotic pump of claim 9, wherein said polymer is selected from the group consisting of cellulose esters and acylated polysaccharides.

11. The osmotic pump of claim 9 wherein said polymer is selected from the group consisting of polyurethanes and polymers of acrylic and methacrylic acid and esters thereof.

12. The osmotic pump of claim 9, wherein said polymer is selected from the group consisting of poly(ortho ester)s and polyacetals.

13. The osmotic pump of claim 1, wherein said pore forming additive is selected from the group consisting of water, alkali metal salts, alkaline earth metal salts, saccharides, aliphatic polyols, aromatic polyols and mixtures thereof.

14. The osmotic pump of claim 1, wherein 0.1 to 50%, by weight, of said pore forming additive is used.

15. The osmotic pump of claim 1, wherein said pH insensitive pore forming additive is selected from the group consisting of polyethylene glycol, sorbitol, glucose and mixtures thereof.

16. The osmotic pump of claim 1, wherein said active agent is selected from the group consisting of potassium chloride, sodium indomethacin trihydrate and cyclobenzaprine HCl.

17. The osmotic pump of claim 1, wherein said active agent is selected from the group consisting of quinoline carboxylic acids, naphthyridine carboxylic acids, pyrimidine carboxylic acids, and cinnoline carboxylic acids.

* * * * *